United States Patent
Goto et al.

(10) Patent No.: US 9,949,711 B2
(45) Date of Patent: Apr. 24, 2018

(54) X-RAY COMPUTED TOMOGRAPHY APPARATUS

(71) Applicant: Toshiba Medical Systems Corporation, Otawara-shi (JP)

(72) Inventors: Takahiro Goto, Utsunomiya (JP); Naruomi Akino, Nasushiobara (JP); Yoshinori Uebayashi, Utsunomiya (JP); Hiroki Taguchi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 74 days.

(21) Appl. No.: 14/926,300

(22) Filed: Oct. 29, 2015

(65) Prior Publication Data
US 2016/0120496 A1 May 5, 2016

(30) Foreign Application Priority Data
Oct. 31, 2014 (JP) ................ 2014-223752
Oct. 28, 2015 (JP) ................ 2015-211763

(51) Int. Cl.
*A61B 6/00* (2006.01)
*A61B 6/03* (2006.01)

(52) U.S. Cl.
CPC .............. *A61B 6/542* (2013.01); *A61B 6/032* (2013.01); *A61B 6/488* (2013.01)

(58) Field of Classification Search
CPC ........... A61B 6/032; A61B 6/542; A61B 6/06; A61B 6/405; A61B 6/482; A61B 6/4021; A61B 6/488; A61B 6/027; A61B 6/035; A61B 6/469; A61B 6/544; A61B 6/4291; A61B 6/4441; A61B 6/503; A61B 6/4078; A61B 6/4085; A61B 6/424; A61B 6/502; A61B 6/481; A61B 6/583; A61B 6/0414; A61B 6/463; A61B 6/465; A61B 6/467; A61B 6/4435; A61B 6/4464; A61B 6/466; A61B 6/0457; A61B 6/4028;
(Continued)

(56) References Cited

U.S. PATENT DOCUMENTS

| 2007/0172020 A1* | 7/2007 | Nambu | A61B 6/032 378/4 |
| 2007/0211859 A1* | 9/2007 | Okada | A61B 6/502 378/97 |
| 2011/0274240 A1* | 11/2011 | Sugaya | A61B 6/032 378/16 |

FOREIGN PATENT DOCUMENTS

| JP | 2003-33346 A | 2/2003 |
| JP | 2008-18044 A | 1/2008 |

(Continued)

*Primary Examiner* — Irakli Kiknadze
(74) *Attorney, Agent, or Firm* — Oblon, McClelland, Maier & Neustadt, L.L.P.

(57) ABSTRACT

An X-ray computed tomography apparatus according to the present embodiment comprises a gantry and a tube current setting circuitry. The tube current setting circuitry set tube currents for the respective imaging regions. To be specific, the tube current setting circuitry calculate X-ray absorption index values in the respective imaging regions, based on scanogram image data, determine tube current values corresponding to the X-ray absorption index values for the respective imaging regions, and correct the tube current values of the respective imaging regions except for a reference region based on a relative relationship between an X-ray absorption index value of the reference imaging region and tube current values of the other imaging regions.

15 Claims, 10 Drawing Sheets

(58) Field of Classification Search
CPC ... A61B 6/4042; A61B 6/4241; A61B 6/4275;
A61B 6/4488; A61B 6/4035
USPC ............... 378/4, 16, 19, 62, 98.8, 98.9
See application file for complete search history.

(56) References Cited

FOREIGN PATENT DOCUMENTS

| | | |
|---|---|---|
| JP | 2009-112627 A | 5/2009 |
| JP | 2009-160394 A6 | 10/2009 |
| JP | 2010-193940 | 9/2010 |
| JP | 2013-66751 A | 4/2013 |
| JP | 2014-61441 A | 4/2014 |
| WO | WO 2010/087267 A1 | 8/2010 |

* cited by examiner

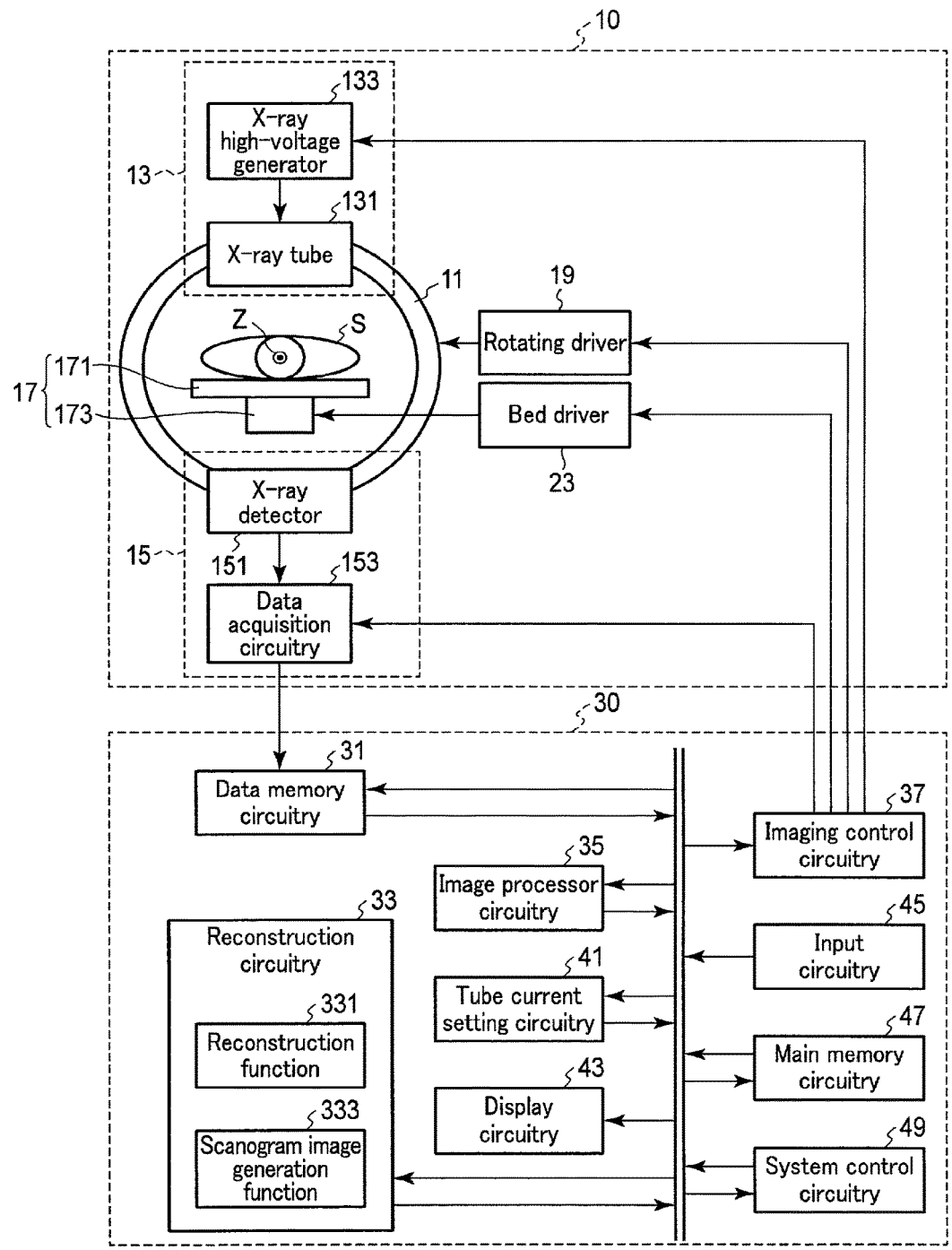
F I G. 1

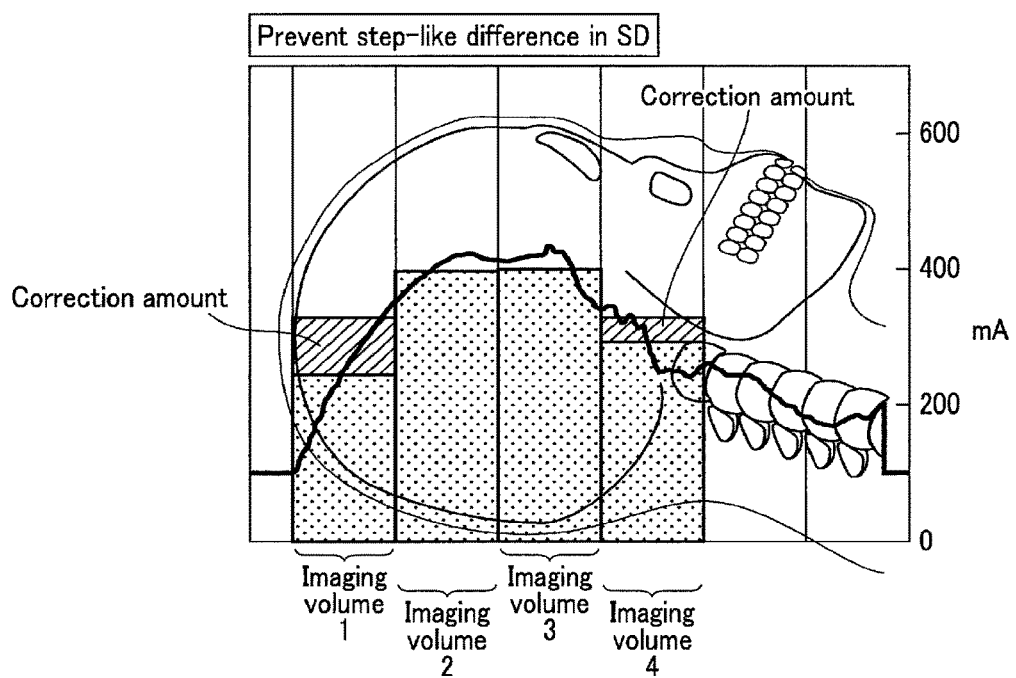
F I G. 5

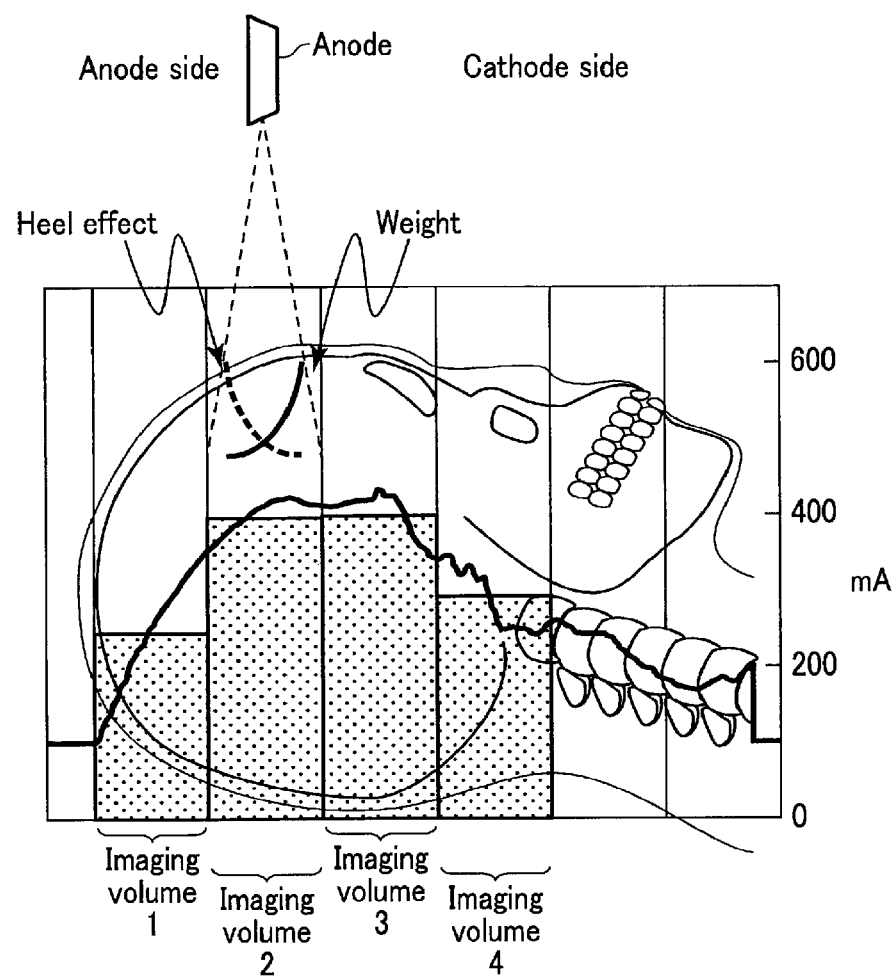
F I G. 11

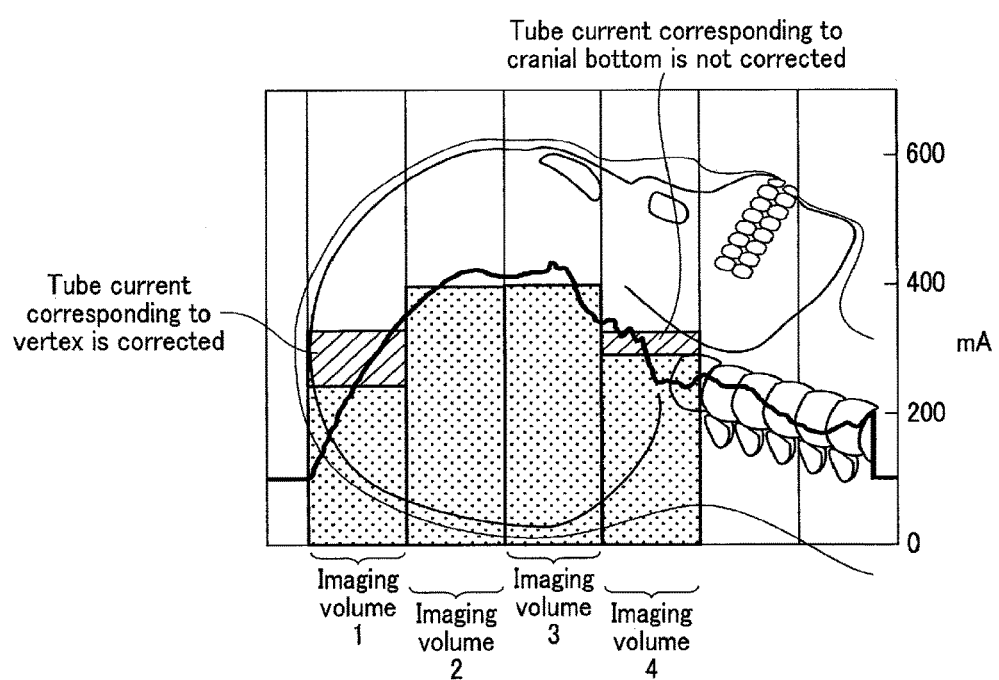
F I G. 12

X-RAY COMPUTED TOMOGRAPHY APPARATUS

CROSS-REFERENCE TO RELATED APPLICATIONS

This application is based upon and claims the benefit of priority from prior Japanese Patent Application No. 2014-223752, filed Oct. 31, 2014 and prior Japanese Patent Application No. 2015-211763, filed Oct. 28, 2015, the entire contents of all of which are incorporated herein by reference.

FIELD

Embodiments described herein relate generally to an X-ray computed tomography apparatus.

BACKGROUND

As technology which is used by an X-ray computed tomography apparatus to automatically set a tube current, auto exposure control (AEC) is known, which automatically determines a tube current in accordance with an X-ray absorption index value, such as a water-equivalent thickness. When the step & shoot process is executed in the AEC to acquire data while moving a top plate intermittently, a tube current value is set for an imaging region regarding each stop position of the top plate. An average value of the X-ray absorption index values of the pixels included in each imaging region is set as an X-ray absorption index value of the imaging region. In the step & shoot process, if there is a rapid shape change, as in the head, the tube current undergoes a step-like change in the adjacent imaging region, causing a difference in an image Standard Deviation (SD). This is attributable to the fact that each image region involves a large number of structures since a recent X-ray computed tomography apparatus employs a larger number of X-ray detectors and the data on a wide range can be acquired at a time.

BRIEF DESCRIPTION OF THE DRAWINGS

FIG. 1 shows a configuration of an X-ray computed tomography apparatus according to the present embodiment.

FIG. 5 is a schematic diagram illustrating the correction processing for a tube current value executed in Step S6 shown in FIG. 2.

FIG. 11 illustrates a weighting of an X-ray absorption amount according to application example 2.

FIG. 12 illustrates a setting of the imaging volume of a correction target according to application example 3.

DETAILED DESCRIPTION

Figure 2:
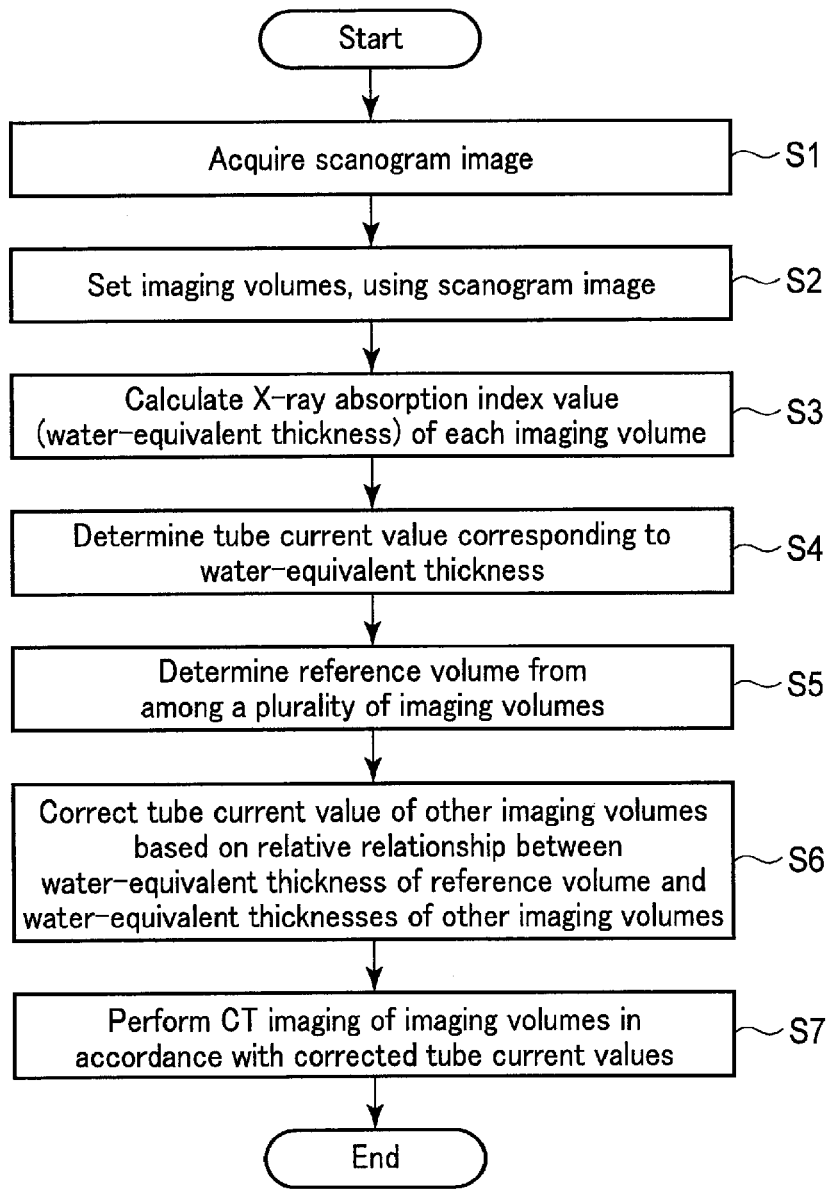
FIG. 2 is a flowchart illustrating a typical operation of the X-ray computed tomography apparatus shown in FIG. 1 performed under the control of a system control circuitry.

An X-ray computed tomography apparatus according to the present embodiment comprises a gantry and a tube current setting circuitry. The gantry is configured in such a manner that an X-ray tube emits an X-ray to a plurality of imaging regions arranged in the body axis direction and an X-ray detector detects the X-rays emitted from the X-ray tube and transmitted through a subject. The tube current setting circuitry set a tube current for each of the imaging regions. To be specific, the tube current setting circuitry calculate first X-ray absorption index values representing the amounts of X-rays absorbed by the subject in the respective imaging regions, based on scanogram image data on the subject in predetermined imaging directions; determine tube current values corresponding to the first X-ray absorption index values for the respective imaging regions; and correct the tube current values of the respective imaging regions except for a reference region based on a relative relationship between an X-ray absorption index value of the reference imaging region and tube current values of the other imaging regions.

An X-ray computed tomography apparatus according to the present embodiment will be described in detail with reference to the accompanying drawings.

FIG. 1 shows a configuration of an X-ray computed tomography apparatus according to the present embodiment. As shown in FIG. 1, the X ray computed tomography apparatus of the present embodiment includes a gantry 10 and a console 30. The gantry 10 supports a rotatable frame 11 having a cylindrical shape in such a manner that the frame 11 can be rotated around the rotation axis Z. An X-ray generating system 13 and an X-ray detecting system 15 are attached to the rotatable frame 11 at positions which face each other with the rotation axis Z therebetween. The opening of the rotating frame 11 is set as a field of view (FOV). Supplied with power from a rotating driver 19, the rotatable frame 11 rotates around the rotation axis Z at a constant angular velocity. The rotating apparatus generates power for rotating the rotatable frame 11 in accordance with control performed by an imaging control circuitry 37 of the console 30. A bed 17 comprises a top plate 171 on which subject S lies and a support base 173 on which the top plate 171 is movably supported. For example, the support base 173 supports the top plate 171 to be movable in the direction of the rotation axis Z, in the vertical direction and the horizontal direction. The support base 173 receives power from a bed driver 23 and moves the top plate 171 in an arbitrary direction. The bed driver 23 moves the top plate 171 in an arbitrary direction in accordance with the control performed by the imaging control circuitry 37.

The X-ray generating system 13 generates X-rays in accordance with a control signal supplied from the imaging control circuitry 37. To be specific, the X-ray generating system 13 comprises an X-ray tube 131 and an X-ray high-voltage apparatus 133. Applied with a high voltage and supplied with a filament current from the X-ray high-voltage circuitry 133, the X-ray tube 131 generates X-rays. The X-ray high-voltage circuitry 133 apply a high voltage to the X-ray tube 131 under control of the imaging control circuitry 37. The X-ray high-voltage circuitry 133 adjust the high voltage applied to the X-ray tube 131 and the filament current supplied to the X-ray tube 131, in such a manner that a predetermined tube voltage value and a predetermined tube current value are maintained.

The X-ray detecting system 15 detects an X-ray generated by the X-ray generating system 13 and transmitted through subject S, and generates digital data in accordance with the intensity of the detected X-ray. To be more specific, the X-ray detecting system 15 comprises an X-ray detector 151 and a data acquisition circuitry 153.

The X-ray detector 151 detects an X-ray generated by the X-ray tube 131. The X-ray detector 151 includes a plurality of X-ray detection elements arranged on a two-dimensional curved plane. Each of the X-ray detection elements detects an X-ray generated by the X-ray tube 131, and generates an electrical signal in accordance with the intensity of the detected X-ray. Each X-ray detection element may be a scintilator detector which is made up of a scintilator and a photoelectric converter and which indirectly converts an X-ray into an electric signal. Alternatively, each X-ray detection may be a semiconductor detector which directly converts an X-ray into an electric signal.

The data acquisition circuitry 153 collect electric signals from the X-ray detection elements for each view and converts the acquired electric signals into digital data. The digital data obtained by the conversion is referred to as raw data. The raw data is a set of digital values representing X-ray intensities which are associated by view numbers that identify the channel numbers and sequence numbers of the related X-ray detection elements and the acquired views. The raw data is supplied to the console 30.

The console 30 comprises a data memory circuitry 31, a reconstruction circuitry 33, an image processor circuitry 35, an imaging control circuitry 37, a tube current setting circuitry 41, a display circuitry 43, an input circuitry 45, a main memory circuitry 47 and a system control circuitry 49.

The data memory circuitry 31 is a storage device for storing raw data supplied from the gantry 10 and is specifically a hard disk drive (HDD) or a solid state drive (SSD).

The reconstruction circuitry 33 include a processor (such as a CPU, an MPU, or a GPU) and a memory (such as a ROM or a RAM) as hardware resources. The reconstruction circuitry 33 read a program stored in the memory and executes it, thereby realizing a reconstruction function 331 and a scanogram image generation function 333.

By the reconstruction function 331, the reconstruction circuitry 33 perform preprocessing (such as logarithmic conversion) for the raw data. The preprocessed data is referred to as projection data. The preprocessing includes various kinds of correction processing, such as logarithmic conversion, X-ray intensity correction, and offset correction. Based on the projection data, the reconstruction circuitry 33 generate a CT image representing the spatial distribution of the CT values of subject S. As an image reconstruction algorithm, an existing image reconstruction algorithm may be used, including an analytical image reconstruction algorithm (such as a filtered back projection (FBP) or a convolution back projection (CBP)) or a statistical image reconstruction algorithm (such as maximum likelihood expectation maximization (ML-EM) or ordered subset expectation maximization (OS-EM)).

By the scanogram image generation function 333, the image reconstruction circuitry 33 generate a scanogram image representing an X-ray projection image of subject S with respect to a predetermined imaging direction (at an angle of rotation around the rotation axis Z), based on raw data acquired by the X-ray detector 15 in a scanography (to be mentioned later) or projection data based on that raw data. To be more specific, the reconstruction circuitry 33 perform filtering processing for the projection data regarding a scanography, thereby generating a scanogram image. Unless the projection data regarding the scanography and the scanogram image have to be discriminated from each other, they will be collectively referred to as scanogram image data. The scanogram image data is used for the automatic tube current setting performed by the tube current setting circuitry 41.

The reconstruction circuitry 33 may include a processing circuitry for the reconstruction function 331 and a processing circuitry for the scanogram image generation function 333.

The image processor circuitry 35 include a processor (such as a CPU, an MPU, or a GPU) and a memory (such as a ROM or a RAM) as hardware resources. The image processor circuitry 35 perform various kinds of image processing for an CT image. For example, the image processor circuitry 35 perform three-dimensional image processing for the CT image, thereby generating a CT image for display. The three-dimensional image processing includes volume rendering, surface rendering, pixel value projection processing, multi-planar reconstruction (MPR), curved planer reconstruction (CPR), or the like.

The imaging control circuitry 37 include a processor (such as a CPU or an MPU) and a memory (such as a ROM or a RAM) as hardware resources. The imaging control circuitry 37 perform overall control of each apparatus installed in the gantry 10. For example, the imaging control circuitry 37 synchronously control the X-ray generating system 13, X-ray detector 15, rotating driver 19 and bed driver 23, so as to perform data acquisition from subject S. The rotating driver 19 rotates at a constant velocity under the control of the imaging control circuitry 37. The X-ray high-voltage apparatus 133 of the X-ray generating system 13 applies a tube voltage having a predetermined tube voltage value to the X-ray generating system 13 under the control of the imaging control circuitry 37. The X-ray high-voltage apparatus 133 also adjusts the tube voltage and the filament current in accordance with the tube current having the predetermined tube current value, under the control of the imaging control circuitry 37. The data acquisition circuitry 153 of the X-ray detector 15 collects raw data for each view in synchronism with the X-ray exposure timing under the control of the imaging control circuitry 37. The imaging control circuitry 37 control the bed driver 23 to move the top plate 171, in accordance with a user's input supplied from an input circuitry 45 (to be mentioned later). For example, the imaging control circuitry 37 synchronously control the X-ray generating system 13, X-ray detector 15, rotating driver 19 and bed driver 23, so as to execute the step & shoot process (which intermittently moves the top plate 171 along the rotation axis Z and performs data acquisition at each stop position of the top plate 171) or the helical scan process (which performs data acquisition while successively moving the top plate 171 along the rotation axis Z). By synchronously controlling the X-ray generating system 13, X-ray detector 15, rotating driver 19 and bed driver 23, the imaging control circuitry 37 can execute a scanography, which performs data acquisition while moving the top plate 171 along the axis Z, with the angle of rotation of the X-ray tube 131 around the axis Z being kept constant.

The tube current setting circuitry 41 include a processor (such as a CPU, an MPU, or a GPU) and a memory (such as a ROM or a RAM) as hardware resources. The tube current setting circuitry 41 automatically set a tube current value based on the scanogram image data, for each of a plurality of imaging regions. A imaging region corresponds to a region from which projection data is acquired while the X-ray tube 131 makes one rotation around the rotation axis Z. In the step & shoot process, in which the top plate 171 is kept stationary during the rotation of the X-ray tube 131, an imaging region corresponds to a stop position of the top plate 171. In the description below, the imaging region will be referred to as an imaging volume. As scanogram image data, projection data acquired by a scanography or a scanogram image may be used.

By executing the tube current setting program stored in the memory, the tube current setting circuitry 41 realize the imaging volume setting function, the X-ray absorption index value calculation function, the tube current determination function, the reference volume determination function and the tube current correction function.

By the imaging volume setting function, the tube current setting circuitry 41 use scanogram image data and sets a plurality of imaging volumes. By the X-ray absorption index value calculation function, the tube current setting circuitry 41 calculate the X-ray absorption index value of subject S based on the scanogram image data, for each of a plurality of imaging volumes. The X-ray absorption index value is an index value reflecting the amount of X-rays absorbed by subject S. To be more specific, the tube current setting circuitry 41 calculate the X-ray absorption index value based on data values at a plurality of data points regarding the related imaging volume of the scanogram image data, for each of a plurality of imaging volumes. What is indicated by the X-ray absorption index value is specifically an X-ray absorption amount, a water-equivalent thickness, an subject thickness, or the like. By the tube current determination function, the tube current setting circuitry 41 initially determine a tube current value corresponding to the X-ray absorption index value by referring to the "X-ray absorption index value vs tube current value table" stored in the main storage circuitry 47. The "X-ray absorption index value vs tube current value table" is a look up table (LUT) or a database in which a plurality of X-ray absorption index values are associated with proper tube current values. Combinations between the X-ray absorption index values and the tube current values are determined beforehand, based on experiment, predictive calculation, clinical knowledge, etc. By the reference volume determination function, the tube current setting circuitry 41 determine a reference volume from among a plurality of imaging volumes, either automatically or in accordance with a user's instruction entered from the input circuitry 45. The reference volume is an imaging volume that is included among a plurality of imaging volumes and that requires highest image quality. By the tube current correction function, the tube current setting circuitry 41 correct the tube current value of an imaging volume based on the relative relationship between the X-ray absorption index value of the reference volume included among the imaging regions and the tube current values of imaging volumes other than the reference volume. The corrected tube current values are stored in the main storage circuitry 47 as setting tube current values.

The display circuitry 43 display various kinds of information on a display device. For example, the display circuitry 43 display a CT image reconstructed by the reconstruction circuitry 33 or a CT image for which image processing is performed by the image processor circuitry 35. The display circuitry 43 may display a scanogram image and a scan plan menu. As the display device, a CRT display, a liquid crystal display, an organic EL display, a plasma display, etc. can be used, as needed.

The input circuitry 45 accept various instructions and information inputs supplied thereto from a user via an input device. For example, the input circuitry 45 accept an imaging start instruction supplied thereto from the user via the input device. As the input device, a keyboard, a mouse, a switch etc. may be used.

The main storage circuitry 47 are a mass storage device (such as an HDD) configured to store various kinds of information. For example, the main storage circuitry 47 stored CT image data, scanogram image data, control programs of an X-ray computed tomography apparatus. The main storage circuitry 47 also store the "X-ray absorption index value vs tube current value table" used by the tube current setting circuitry 41.

The system control circuitry 49 include a processor (such as a CPU or an MPU) and a memory (such as a ROM or a RAM) as hardware resources. The system control circuitry 49 serve as the nerve center of the X-ray computed tomography apparatus. To be specific, the system control circuitry 49 read the control program stored in the main storage circuitry 47, expands it in a memory, and controls the respective units of the X-ray computed tomography apparatus in accordance with the expanded control program.

A description will now be given of an example of an operation which the X-ray computed tomography apparatus performs under the control of the system control circuitry 49. To give specific descriptions below, it is assumed that the X-ray absorption index value is a water-equivalent thickness, the imaging method used for setting a tube current is the step & shoot process, and scanogram image data is a scanogram image.

FIG. 2 is a flowchart illustrating a typical operation which the X-ray computed tomography apparatus performs under the control of the system control circuitry 49.

As shown in FIG. 2, the system control circuitry 49 cause the imaging control circuitry 37 to execute a scanography (Step S1) as a pre-stage preceding the imaging of the step & shoot process (Step S1). In Step S1, the imaging control circuitry 37 control the X-ray generating system 13, X-ray detector 15, rotating driver 19 and bed driver 23 to perform a positional scan, for example in accordance with a user's instruction supplied via the input circuitry 45. To be more specific, the imaging control circuitry 37 control the rotating driver 19 and rotates the rotatable frame 11 around the rotation axis Z in such a manner that the X-ray tube 131 is arranged in a desired imaging direction (at an angle of rotation around the rotation axis Z). The imaging direction of the X-ray tube 131 can be arbitrarily determined in accordance with a user's instruction entered via the input circuitry 45. In addition, the imaging control circuitry 37 control the bed driver 23, X-ray high-voltage apparatus 133, and data acquisition circuitry 153, and moves the top plate 171 along the rotation axis Z while simultaneously permitting the X-ray tube 131 arranged in the imaging direction to generate X-rays. In this manner, the data acquisition circuitry 153 are made to collect projection data regarding the imaging direction. As a result, a positional scan is performed for the imaging range of a subject, using X-rays. The imaging range regarding the scanography is determined in such a manner as to include the imaging range of the imaging performed in Step S7. The projection data regarding the positioning imaging is transmitted to the console 30. A scanogram image is generated by the reconstruction circuitry 33 based on the projection data.

After the execution of Step S1, the system control circuitry 49 cause the tube current setting circuitry 41 to execute Steps S2, S3, S4, S5 and S6 mentioned below.

In Step S2, the tube current setting circuitry 41 execute the imaging volume setting function. By the imaging volume setting function, the tube current setting circuitry 41 use a scanogram image and sets a plurality of imaging volumes along the rotation axis Z in the imaging range of the imaging. For example, the tube current setting circuitry 41 set a plurality of imaging volumes in accordance with user's instructions entered on a scanogram image and supplied via the input circuitry 45.

After the execution of Step S2, the tube current setting circuitry 41 execute the X-ray absorption index value calculation function. By the X-ray absorption index value calculation function, the tube current setting circuitry 41 calculate an X-ray absorption index value (a water-equivalent thickness) for each imaging volume (Step S3). To be specific, the tube current setting circuitry 41 calculate a water-equivalent thickness based on pixel values of a plurality of pixels regarding the related image region corresponding to the imaging volume included in the scanogram image, for each of a plurality of imaging volumes. To be more specific, for each of the pixels in the image region, an X-ray absorption amount is calculated based on the pixel value, and a water-equivalent thickness corresponding to the calculated X-ray absorption amount is obtained using a predetermined conversion formula. The water-equivalent thickness is a water-equivalent thickness regarding the imaging direction of the scanogram image. A statistical value of the water-equivalent thicknesses regarding the pixels included in each imaging volume is determined as a water-equivalent thickness representative of the imaging volume. The statistical value is, for example, an average value of the water-equivalent thicknesses regarding a plurality of pixels, an intermediate value thereof, or the like. To give specific descriptions below, it is assumed that the statistical value is an average value, and the water-equivalent thickness representative of the imaging volume will be referred to as an average water-equivalent thickness.

After the execution of Step S3, the tube current setting circuitry 41 execute the tube current determination function. By the tube current determination function, the tube current setting circuitry 41 initially determine a tube current value corresponding to the average water-equivalent thickness, using the "X-ray absorption index value vs tube current value table" (Step S4).

Figure 3:
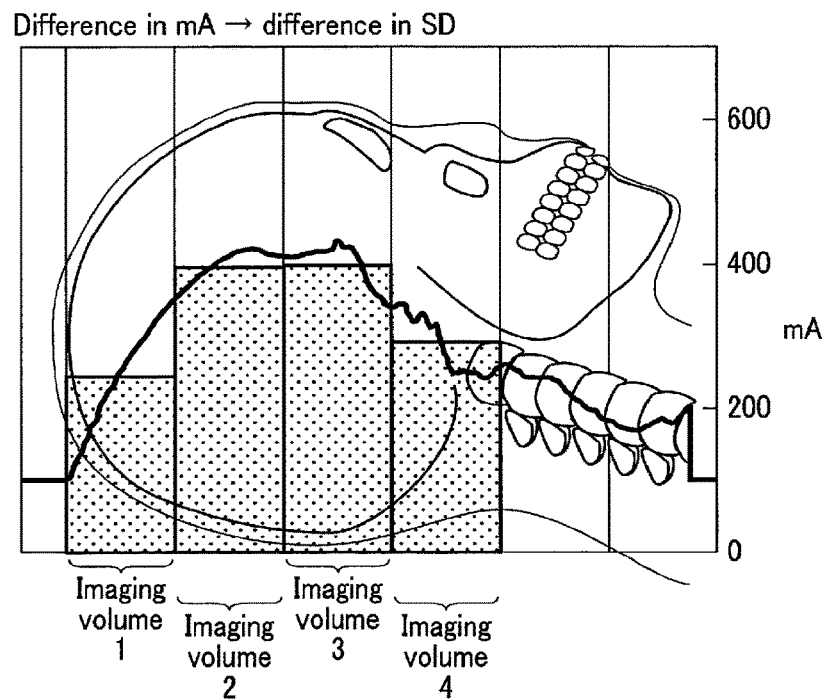
FIG. 3 is a schematic diagram illustrating the initial determination processing for a tube current value executed in Step S4 shown in FIG. 2.
Figure 4:
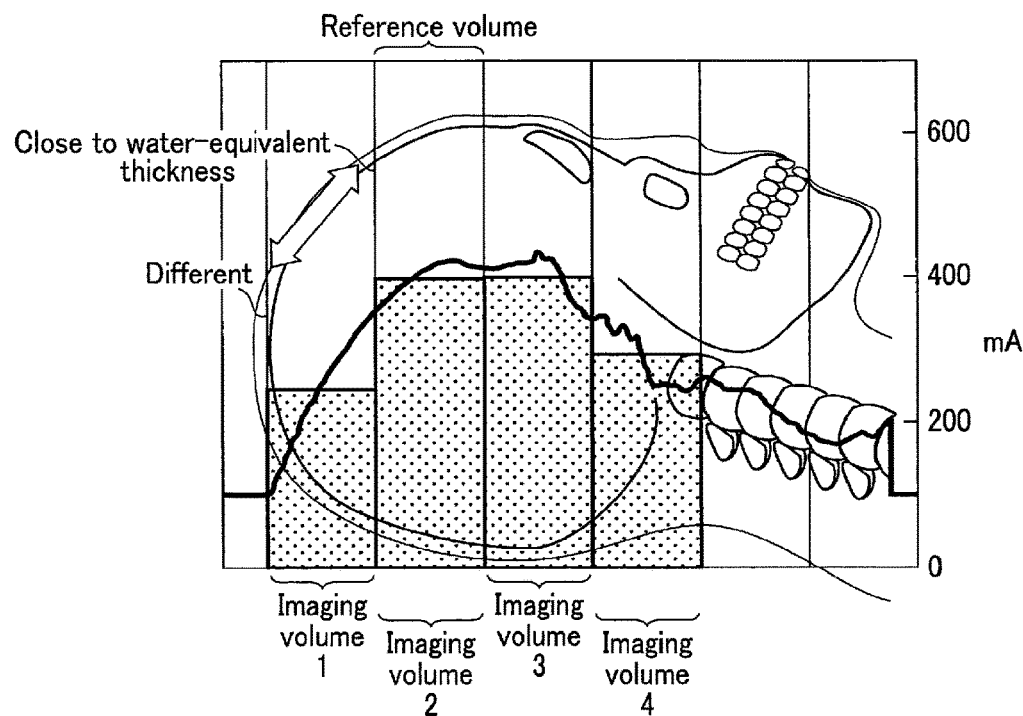
FIG. 4 is a schematic diagram illustrating the determination processing for a reference volume executed in Step S5 shown in FIG. 2.

FIG. 3 is a schematic diagram illustrating how the initial determination processing for determining a tube current value is executed in Step S4. As depicted in FIG. 3, a plurality of imaging volumes are set along the rotation axis Z in the scanogram image. In FIG. 3, the bold line indicates a tube current value [mA] for each Z coordinate, and the bar graph shown as a dot hatching indicates tube current value [mA] for each imaging volume. The tube current value for each Z coordinate is not used in practice. The tube current value for each Z coordinate is a tube current value determined by applying the "X-ray absorption index value vs tube current value table" to the average value of the water-equivalent thicknesses regarding the Z coordinates. The tube current value for each imaging volume represents an average value of the tube current values measured at a number of angles of rotation of the X-ray tube 131 when the X-ray tube 131 makes one rotation around the imaging volume. In the present embodiment, the directional modulation of the tube current is not taken into consideration. As shown in FIG. 3, the object thickness varies greatly along the rotation axis Z in the head region. In the meantime, the tube current value of each imaging volume is determined based on the average value of the water-equivalent thicknesses of the pixels included in the imaging volume. Therefore, as shown in FIG. 4, the thicknesses of the imaged object may be close to each other at the border between the first imaging volume and the second imaging volume, but at the other end, the thickness of the imaged object of the first imaging volume differs greatly from the imaged object of the second imaging volume. Where a tube current value is determined based on an average water-equivalent thickness, the tube current value differs greatly between the first imaging volume and the second imaging volume, resulting in a large difference in the image SD.

To solve the step-like difference in the image DS, the tube current setting circuitry 41 of the present embodiment correct the tube current values of a plurality of imaging volumes by executing the processing of Steps S5 and S6, After the execution of Step S4, the tube current setting circuitry 41 execute the reference volume determination function. By the reference volume determination function, the tube current setting circuitry 41 determine a reference volume from among a plurality of imaging volumes (Step S5).

FIG. 4 is a schematic diagram illustrating how the processing for determining a reference volume is executed in Step S5. As described above, the reference volume is an imaging volume that is included among a plurality of imaging volumes and that requires highest image quality. Typically, an imaging volume having the greatest water-equivalent thickness is used as the reference volume. In this case, the tube current setting circuitry 41 automatically determine the imaging volume having the greatest water-equivalent thickness as the reference volume, based on the water-equivalent thicknesses of a plurality of imaging volumes. The reference volume can be an arbitrary one that is selected from a plurality of imaging volumes based on a user's instruction entered from the input circuitry 45. To give specific descriptions below, it is assumed that an imaging volume having the greatest water-equivalent thickness is used as the reference volume.

After the execution of Step S5, the tube current setting circuitry 41 execute the tube current correction function. By the tube current correction function, the tube current setting circuitry 41 correct the tube current value of an imaging volume based on the relative relationship between the water-equivalent thickness of the reference volume and the water-equivalent thicknesses of imaging volumes other than the reference volume (Step S6). The corrected tube current value is stored in the main storage circuitry 47 as a setting tube current value, for each of the imaging volumes.

FIG. 5 is a schematic diagram illustrating how the correction processing for correcting a tube current value is executed in Step S6. As shown in FIG. 5, the tube current setting circuitry 41 correct the tube current values of the respective imaging volumes to make them closer to the tube current value of the reference volume in such a manner that a step-like difference is not caused between the image SD of the reference volume and the image SDs of the other imaging volumes. In the present embodiment, the reference volume is an imaging volume which is included in a plurality of imaging volumes and which has the greatest water-equivalent thickness. Therefore, the tube current values of the other imaging volumes are increased. To be specific, the tube current setting circuitry 41 adjust the water-equivalent thicknesses based on weights determined in accordance with the relative relationships of the respective imaging volumes with the reference volume, and determines tube current values corresponding to the adjusted water-equivalent thicknesses. A specific method for adjusting a water-equivalent thickness will be described below.

Figure 6:
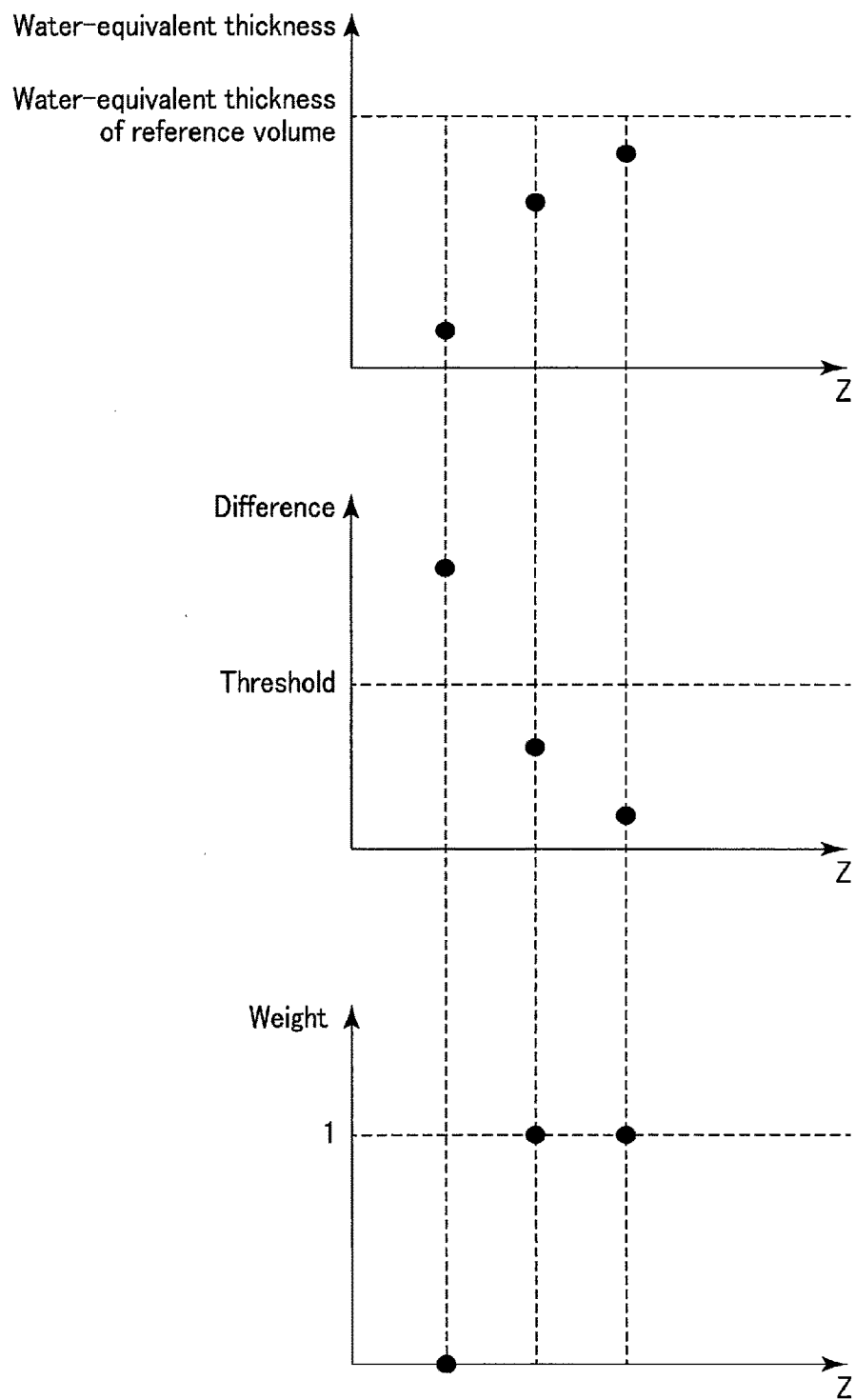
FIG. 6 illustrates an adjustment method for a first water-equivalent thickness performed by tube current setting circuitry in Step S6 shown in FIG. 2.

FIG. 6 illustrates how a first water-equivalent thickness is adjusted. In the upper portion, FIG. 6 shows a graph representing how the water-equivalent thickness of the imaging volume to be processed changes with respect to the Z axis. In the middle portion, FIG. 6 shows a graph representing how the difference of the water-equivalent thickness of the imaging volume to be processed relative to the water-equivalent thickness of the reference imaging volume changes with respect to the Z axis. In the lower portion, FIG. 6 shows a graph representing how a weight value corresponding to the difference is determined with respect to the Z axis. As shown in FIG. 6, the tube current setting circuitry 41 compare the water-equivalent thickness of each of the pixels of the imaging volume to be processed with the average water-equivalent thickness of the reference volume, and calculates a differential value between the water-equivalent thickness related to each of the pixels and the average water-equivalent thickness of the reference volume. The tube current setting circuitry 41 determine a weight value corresponding to the differential value with respect to the Z coordinate, for each of the pixels, and applies the determined weight value to the water-equivalent thickness related to the pixel. The larger the differential value is, the smaller the weight value is set. For example, as shown in the middle portion of FIG. 6, the tube current setting circuitry 41 determine a threshold value of the differential value, and as shown in the lower portion of FIG. 6, the weight value of the pixel having a differential value larger than the threshold value is set to be smaller than the weight value of the pixel having a differential value smaller than the threshold value. For example, the weight value of the pixel having a differential value larger than the threshold value may be set to be "zero", and the weight value of the pixel having a differential value smaller than the threshold value may be set to be "1." The weight value, thus determined, is applied to the water-equivalent thickness related to the pixel, and the water-equivalent thickness related to the pixel is thereby adjusted. An adjusted average water-equivalent thickness of the imaging volume is calculated based on the adjusted water-equivalent thicknesses of a plurality of pixels. The tube current setting circuitry 41 determine a tube current value corresponding to the adjusted average water-equivalent thickness, using the "X-ray absorption index value vs tube current value table." In this manner, the tube current value can be corrected in accordance with the differential value between the average water-equivalent thickness related to each of the imaging volume and the average water-equivalent thickness of the reference volume.

As described above, in the method for adjusting the first water-equivalent thickness, the tube current setting circuitry 41 compare the water-equivalent thickness of each of the pixels of each imaging volume with the average water-equivalent thickness of the reference volume, and adjusts the average water-equivalent thickness, using a weight value determined in accordance with a differential value between the water-equivalent thickness related to each of the pixels and the average water-equivalent thickness of the reference volume. The weight value is dependent on the relative relationship between the water-equivalent thickness of each imaging volume and the water-equivalent thickness of the reference volume. In the present embodiment, a weight value, which is in inverse proportion to a differential value, is applied to the water-equivalent thickness regarding a pixel. Therefore, the adjusted average water-equivalent thickness is larger than the unadjusted average water-equivalent thickness. In other words, the average water-equivalent thickness of each imaging volume can be represented in the unadjusted (or original) average water-equivalent thickness of the imaging volume, and yet can be made closer to the average water-equivalent thickness of the reference volume. Accordingly, the step-like difference in the tube current values between imaging volumes can be properly reduced, while maintaining the magnitude relationship of the water-equivalent thicknesses between the imaging volumes.

Figure 7:
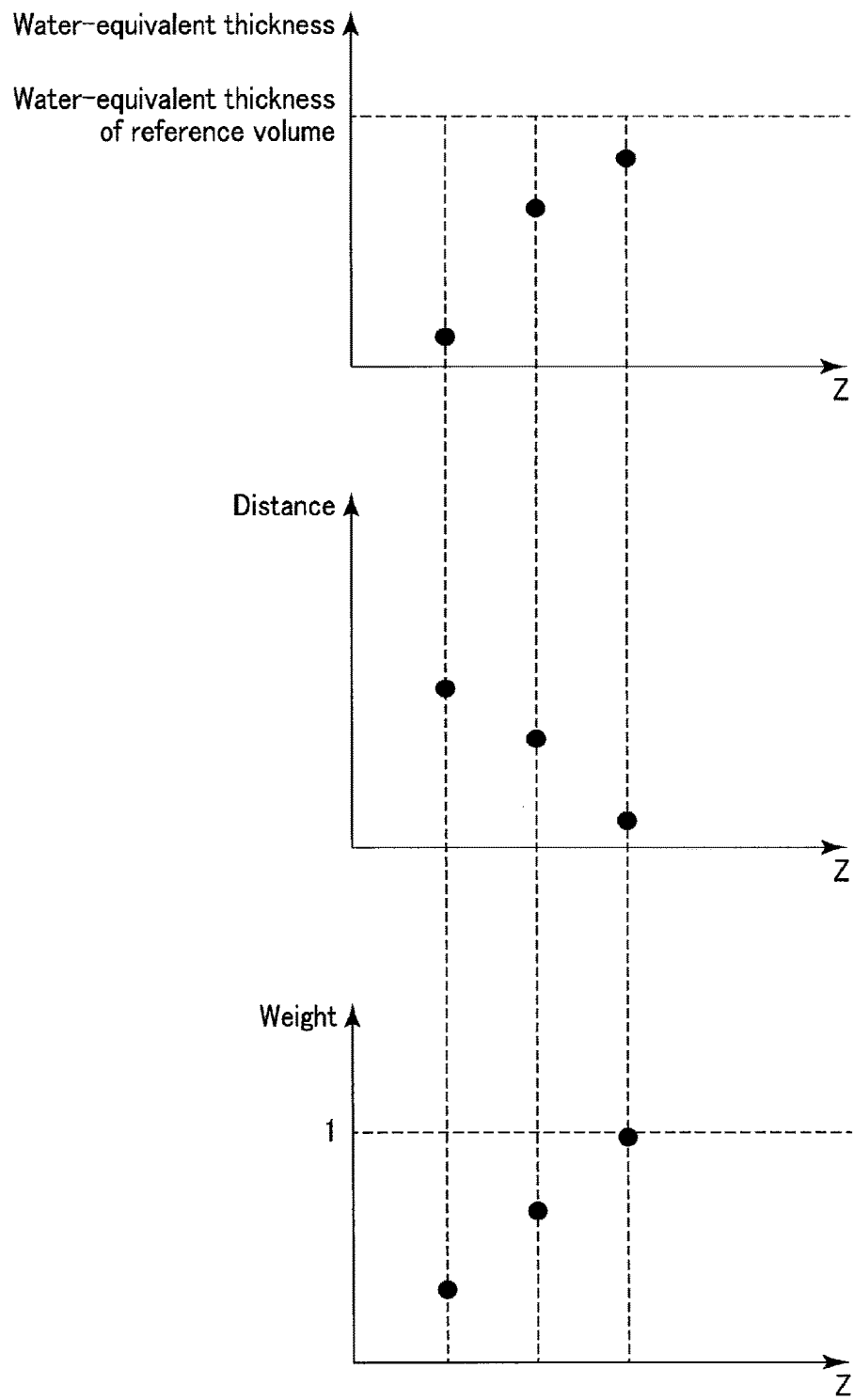
FIG. 7 illustrates an adjustment method for a second water-equivalent thickness performed by the tube current setting circuitry in Step S6 shown in FIG. 2.

FIG. 7 illustrates how a second water-equivalent thickness is adjusted. In the upper portion, FIG. 7 shows a graph representing how the water-equivalent thickness of the imaging volume to be processed changes with respect to the Z axis. In the middle portion, FIG. 7 shows a graph representing how the distance to the reference volume changes with respect to the Z axis. In the lower portion, FIG. 7 shows a graph representing how a weight value corresponding to the distance is determined with respect to the Z axis. As shown in FIG. 7, the tube current setting circuitry 41 calculate distances between Z coordinates of pixels of an imaging volume to be processed and the Z coordinate of a reference point of a reference volume. The reference point of the reference volume may be, for example, an end point of the reference volume as determined on the Z axis, an intermediate point thereof, or an arbitrary point thereof. The tube current setting circuitry 41 determine a weight value corresponding to the distance between each of the Z coordinates of the pixels and the Z coordinate of the reference point, and applies the determined weight value to the water-equivalent thickness related to the pixel. The longer the distance is, the smaller the weight value is set. The weight values may be determined linearly in inverse proportion to the distances. Alternatively, they may be determined nonlinearly using a multidimensional function dependent on distances. The weight value, thus determined, is applied to the water-equivalent thickness related to the pixel, and the water-equivalent thickness related to the pixel is thereby adjusted. An adjusted average water-equivalent thickness (e.g., an average value) of the imaging volume is calculated based on the adjusted water-equivalent thicknesses of a plurality of pixels. The tube current setting circuitry 41 determine a tube current value corresponding to the adjusted average water-equivalent thickness, using the "X-ray absorption index value vs tube current value table." In this manner, the tube current value can be corrected in accordance with the distance between the reference volume and each imaging volume.

As described above, in the method for adjusting the second water-equivalent thickness, the tube current setting circuitry 41 calculate a distance between each of the pixels of each imaging volume and the reference volume, and adjusts the average water-equivalent thickness for each of the pixels, using a weight value determined in accordance with the distance. In general, the water-equivalent thickness of each imaging volume becomes less related to the water-equivalent thickness of the reference volume, in accordance with an increase in the distance to the reference volume. Therefore, the weight value is dependent on the relative relationship between the water-equivalent thickness of each imaging volume and the water-equivalent thickness of the reference volume. In the present embodiment, a weight value, which is in inverse proportion to a distance, is applied to the water-equivalent thickness regarding a pixel. Therefore, the adjusted average water-equivalent thickness is larger than the unadjusted average water-equivalent thickness. In other words, the average water-equivalent thickness of each imaging volume can be represented in the unadjusted (or original) average water-equivalent thickness of the imaging volume, and yet can be made closer to the average water-equivalent thickness of the reference volume. As described above, the tube current value is determined in accordance with the average water-equivalent thickness. Accordingly, the step-like difference in the tube current values between imaging volumes can be properly reduced, while maintaining the magnitude relationship of the water-equivalent thicknesses between the imaging volumes.

In this manner, the tube current setting circuitry 41 complete the setting processing of the tube current.

After Step S6, the system control circuitry 49 cause the imaging control circuitry 37 to perform imaging. In Step S7, the imaging control circuitry 37 synchronously control the X-ray generating system 13, X-ray detector 15, rotating driver 19 and bed driver 23, so as to perform the step & shoot process. At this time, the imaging control circuitry 37 perform CT imaging of each imaging volume in accordance with the tube current value determined for each imaging volume (Step S6). The raw data regarding each imaging volume is transmitted to the console 30. The reconstruction circuitry 33 reconstruct a CT image related to each imaging volume, based on the raw data on the imaging volume. The reconstructed CT image is displayed by the display circuitry 43.

As described above, the X-ray computed tomography apparatus performs an operation under the control of the system control circuitry 49.

In the above description, the correction amount of the tube current value, namely, the differential value between the unadjusted tube current value and the adjusted tube current value, is not restricted. However, the present embodiment is not limited to this. That is, there may be an upper limit to the correction amount of the tube current value. In this case, when determining a corrected tube current value, the tube current setting circuitry 41 determine whether the correction amount is greater than the upper limit. If the correction amount is smaller than the upper limit, the tube current setting circuitry 41 use the corrected tube current value as a final tube current value. If the correction amount is larger than the upper limit, the tube current setting circuitry 41 add the value of the upper limit to the uncorrected tube current value or subtracts that value from the uncorrected tube current value, and uses the resultant value as a final tube current value. In this manner, the tube current setting circuitry 41 limit the correction amount (by which an uncorrected tube current value is changed to a corrected tube current value) to be less than the upper limit value described above. The upper limit value may be determined beforehand in accordance with the body portions to be examined. If an upper limit value is determined for each of the body portions to be examined, the correction amount can be controlled to be a proper value in consideration of the sensitivity to X-rays of each body portion to be examined.

In connection with the tube current setting processing performed by the tube current setting circuitry 41 of the above-mentioned embodiment, reference was made to the case where the Step & shoot process is used. However, the present embodiment is applicable to the helical scan process as well. Where the tube current setting in the helical scan process is performed, the imaging region should be defined in relation to the data acquisition region from which data is acquired while the X-ray tube 131 makes one rotation around the rotation axis Z. With the imaging region defined as above, the tube current setting processing can be performed in the helical scan process, as it is in the step & shoot process.

In the above-mentioned embodiment, it is assumed that the X-ray computed tomography apparatus is a third-generation apparatus. In other words, it is assumed that the X-ray computed tomography apparatus is a rotate/rotate-type, wherein the X-ray tube 131 and the X-ray detector 151 integrally rotate around the rotation axis Z. However, the X-ray computed tomography apparatus of the embodiment is not limited to this. For example, the X-ray computed tomography apparatus may be a stationary/rotate-type, wherein a large number of X-ray detection elements annularly arranged are kept stationary, and only the X-ray tube 131 is rotated around the rotation axis Z.

As described above, the X-ray computed tomography apparatus of the present embodiment comprises a gantry 10 and a tube current setting circuitry 41. The gantry 10 is configured in such a manner that an X-ray tube 131 emits an X-ray to a plurality of imaging regions arranged in the body axis (rotation axis Z) direction and an X-ray detector 151 detects the X-rays emitted from the X-ray tube 131 and transmitted through subject S. The tube current setting circuitry 41 calculate X-ray absorption index values representing the amounts of X-rays absorbed by subject S in the respective imaging volumes, based on scanogram image data on the subject in predetermined imaging directions. Next, the tube current setting circuitry 41 determine tube current values corresponding to the X-ray absorption index values for the respective imaging regions. Then, the tube current setting circuitry 41 correct the tube current values of imaging regions other than a reference imaging region of the plurality of imaging regions, based on relative relationships between the X-ray absorption index values of the reference imaging region and the X-ray absorption index values of the imaging regions other than the reference imaging region.

With the above structure, even if the imaging volume covers a wide range, a step-like difference in the tube current value can be suppressed in relation to the tube current value of the adjacent imaging volumes, because the relative relationships between the water-equivalent thickness of the reference volume and the water-equivalent thicknesses of the other imaging volumes are taken into consideration. Since the step-like difference in the tube current value can be suppressed, a step-like difference in the image SD can be suppressed between imaging volumes.

APPLICATION EXAMPLE 1

In the above-mentioned embodiment, the directional modulation of the tube current is not taken into consideration. In application example 1 of the present embodiment, the tube current is directionally modified.

Figure 8:
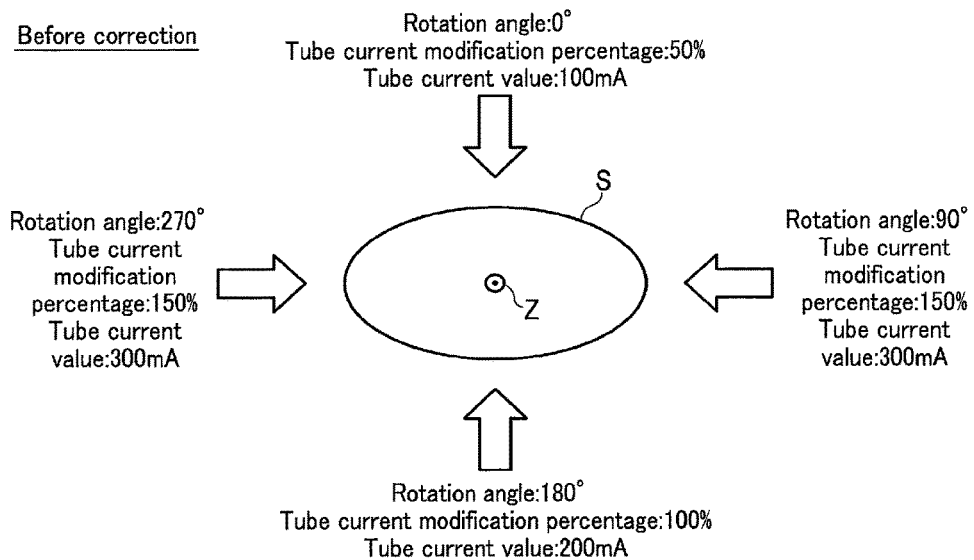
FIG. 8 illustrates a directionally modulation for a tube current according to application example 1 of the present embodiment, specifically shows an assignment of a tube current value before the tube current setting circuitry correct the tube current.

FIG. 8 illustrates how a tube current is directionally modified and shows how a tube current value is assigned before the tube current setting circuitry 41 correct the tube current. In FIG. 8, it is assumed that the setting tube current value is 200 mA. As shown in FIG. 8, in the directional modulation, a modulation degree of the tube current value (reference tube current value: 200 mA) is assigned to each angle of rotation at which the X-ray tube 131 rotates around the rotation axis Z. Typically, the modulation degree of the tube current value is expressed as a percentage, with the setting tube current value of 200 mA being expressed as 100%. This percentage will be referred to as a tube current modulation percentage. The tube current setting circuitry 41 assign a tube current modulation percentage to each angle of rotation in such a manner that an average value of the tube current values assigned to the respective angles of rotation becomes equal to the setting tube current value. Typically, the tube current modulation percentage is increased in accordance with an increase in the water-equivalent thickness, and is decreased in accordance with a decrease in the water-equivalent thickness. Typically, the same tube current value is assigned to the angles of rotation that are opposed to each other, with the Z axis interposed. For example, as shown in FIG. 8, the tube current modulation percentage assigned to the rotation angle of 90° and the tube current modulation percentage assigned to the rotation angle of 270° are both 150%. If consideration is given only to the water-equivalent thickness, the same tube current modulation percentage is assigned to the rotation angle of 0° and the rotation angle of 180°. However, it is presumed that an anatomical body portion which is influenced by X-rays is located at the position facing the rotation angle of 0°. In this case, if X-rays are emitted at the angle of rotation of 0° and the tube current value is set based on the tube current modulation percentage corresponding to the water-equivalent thickness, then a high dose of X-rays will be applied to the anatomical body portion. Where the angles of rotation include a specific angle of rotation facing an anatomical body portion that is greatly influenced by X-rays, the tube current setting circuitry 41 assign a tube current modulation percentage lower than a reference tube current modulation percentage to the predetermined angle of rotation. To compensate for the reduction of the tube current at the predetermined angle of rotation, the tube current setting circuitry 41 assign a tube current modulation percentage higher than the reference tube current modulation percentage to the angle of rotation opposed to the predetermined angle of rotation.

Figure 9:
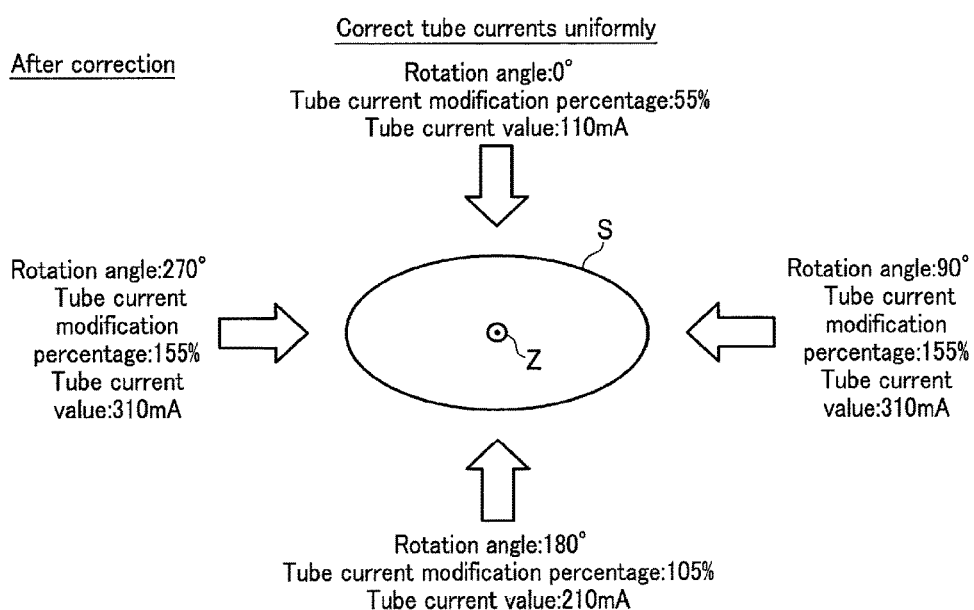
FIG. 9 illustrates a directionally modulation for a tube current according to application example 1, specifically shows an assignment of the tube current values if the tube current setting circuitry uniformly correct the tube current values without reference to the angles of rotation.

FIG. 9 illustrates how a tube current is directionally modified and shows how the tube current setting circuitry 41 uniformly correct the tube current values without reference to the angles of rotation. The setting tube current values shown in FIG. 9 are larger than those shown in FIG. 8 by 10 mA. Where the tube current values are uniformly corrected without reference to the angels of rotation, the tube current setting circuitry 41 increase the tube current values corresponding to all angles of rotation. In the example shown in FIG. 9, the tube current values are increased by 10 mA.

Figure 10:
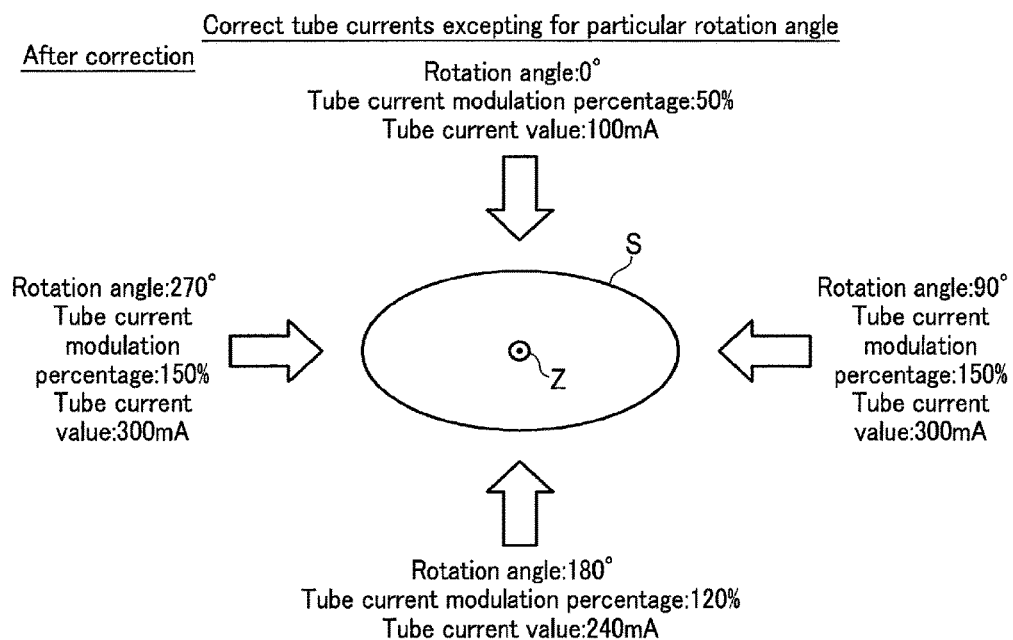
FIG. 10 illustrates a directionally modulation for a tube current according to application example 1, specifically shows an assignment of the tube current values if the tube current setting circuitry correct the tube current values peculiarly for each angle of rotation.

FIG. 10 illustrates how a tube current is directionally modified and shows how the tube current setting circuitry 41 of the above embodiment corrects the tube current values peculiarly for each angle of rotation and assigns the corrected tube current values. Like the tube current values shown in FIG. 9, the setting tube current values shown in FIG. 10 are larger than those shown in FIG. 8 by 10 mA. In this case, the tube current setting circuitry 41 do not correct the tube current value corresponding to the angle of rotation facing an anatomical body portion greatly influenced by X-rays but corrects the tube current values corresponding to the other angles of rotation. In this case, the tube current setting circuitry 41 calculate correction amounts corresponding to the angles of rotation other than the predetermined angle of rotation, namely, changes in the tube current modulation percentage, in such a manner that the average value of the tube current values corresponding to all angles of rotation becomes equal to the setting tube current value. The angles of rotation at which the tube current values are corrected may be all angles of rotation, except the predetermined angle of rotation; alternatively, they may some of the angles of rotation. For example, as shown in FIG. 10, let us assume that the tube current value at the angle of rotation of 180° opposed to the predetermined angle of rotation (0°) is increased. In this case, a tube current modulation percentage of 120% is assigned to the angle of rotation of 180° so that the average value of the tube current values corresponding to all angles of rotation becomes equal to the setting tube current value of 210 mA.

As described above, in the directional modulation of the tube current value, the tube current setting circuitry 41 according to application example 1 correct the tube current values corresponding to the angles of rotation other than the predetermined angle of rotation facing the anatomical body portion greatly influenced by X-rays. Accordingly, the amount of X-rays applied to an anatomical body portion which may be greatly influenced by the X-rays can be reduced, and yet the tube current value for each imaging volume can be increased.

In the above description, the differential value between the tube current values set for opposite angels of rotation is not restricted. However, the present embodiment is not limited to this. That is, an upper limit may be determined for the differential value between the tube current values set for opposite angels of rotation. In this case, when determining a corrected tube current value, the tube current setting circuitry 41 determine whether the differential value between the tube current values set for the opposite angles of rotation is greater than the upper limit. If the differential value is smaller than the upper limit, the tube current setting circuitry 41 use the corrected tube current value as a final tube current value. If the differential value is larger than the upper limit, the tube current setting circuitry 41 maintain the tube current value set for the predetermined angle of rotation facing an anatomical body portion which may be greatly influenced by X-rays, but adds the value of the upper limit to the uncorrected tube current value at the angle of rotation opposite the predetermined angle of rotation and uses the resultant value as a final tube current value. If the average value of the tube current values corresponding to all angles of rotation does not become equal to the setting tube current value, the current value corresponding to the deficiency may be added to the tube current values at other angles of rotation. In this manner, the tube current setting circuitry 41 limit the differential value between the tube current values corresponding to the opposite angles of rotation to be less than the upper limit value. The upper limit value may be determined beforehand in consideration of the image quality of a CT image or the like.

APPLICATION EXAMPLE 2

In Step S3 shown in FIG. 2, the tube current setting circuitry 41 calculate the water-equivalent thickness of each imaging volume without considering the X-ray hardening caused by the heel effect. According to application example 2, the tube current setting circuitry 41 calculate the water-equivalent thickness of each imaging volume in due consideration of the X-ray hardening caused by the heel effect. To be specific, the tube current setting circuitry 41 weight the X-ray absorption amount at each pixel of each imaging volume using a weight value determined in consideration of the X-ray hardening caused by the heel effect.

FIG. 11 illustrates how each pixel of each imaging volume is weighted according to application example 2. FIG. 11 is a scanogram image showing a side portion of a subject, and a graph showing how a water-equivalent thickness changes with respect to the Z axis, a curve indicating the heel effect, and a curve indicating the weight value are superimposed on the scanogram image. In FIG. 11, it is assumed that imaging volume 2 is processed.

The X-ray tube 131 is provided with an anode, as shown in FIG. 11, and with a cathode (not shown). The anode and the cathode are on the Z-axis. An X-ray is generated by the interaction of thermal electrons coming from the cathode and the material constituting the anode, and the X-ray is emitted from the anode. It is known in the art that the longer the traveling path of an X-ray inside the anode, the harder the X-ray becomes. The anode is designed in such a manner that its diameter increases along the Z axis from the cathode side to the anode side. Therefore, X-rays emitted from the anode are hard on the anode side and are soft on the cathode side. This phenomenon is referred to as the heel effect.

The tube current setting circuitry 41 calculate X-ray absorption amounts with respect to respective pixels included in each of imaging volumes, and determines weight values of the X-ray absorption amounts such that they are greater at positions where the X-rays are not hard than at positions where they are hard due to the heel effect. Since the weight values compensate for variations in the pixel values or X-ray absorption amounts which may be caused by the heel effect, they are set at small values where the X-ray hardening caused by the heel effect is marked, and set at large values where the X-ray hardening caused by the heel effect is not so marked. In other words, the weight values are larger for those pixels located far from the anode in the Z-axis direction and are smaller for those pixels located near the anode in the Z-axis direction. The weight values may be calculated by the tube current setting circuitry 41 based on the amounts of X-rays actually measured; alternatively, they may be entered via the input circuitry 45.

After the weighting, the tube current setting circuitry 41 calculate the water-equivalent thickness of an imaging volume to be processed, based on the weighted X-ray absorption amounts of imaging volumes, by using a similar method to that described in Step S3. To be specific, the tube current setting circuitry 41 convert each weighted X-ray absorption amount into a water-equivalent thickness according to a predetermined conversion formula, and determines the water-equivalent thickness of each imaging volume based on the water-equivalent thicknesses regarding the pixels included in each imaging volume.

As described above, according to application example 2, the weight values are set as being larger for those pixels which are not much affected due to the heel effect, and set as being smaller for those pixels which are affected due to the heel effect.

In the above description, a weight value is determined for the X-ray absorption amount of each pixel, but the present embodiment is not limited to this. For example, the tube current setting circuitry 41 may determine a weight value for the pixel value of each of the pixels included in each imaging volume. In this case, an X-ray absorption amount is calculated for each of the pixels, based on the weighted pixel values.

APPLICATION EXAMPLE 3

In the embodiment described above, reference was made to the case where the tube current value is corrected for all imaging volumes other than the reference volume. However, the present embodiment is not limited to this. According to application example 3, the tube current setting circuitry 41 correct the tube current value only with respect to an imaging volume which is included in a plurality of imaging volumes and which is to be corrected.

FIG. 12 illustrates how the imaging volume of correction target is set according to application example 3. As shown in FIG. 12, the tube current setting circuitry 41 select an imaging volume of clinical interest from a plurality of imaging volumes other than the reference volume, and sets the selected imaging volume as a correction target. For example, if the vertex portion of the head is of more clinical interest than the cranial portion of the head, imaging volume 1 corresponding to the vertex portion is determined as a correction target.

The tube current setting circuitry 41 may be configured such that an imaging volume to be corrected is selected based on a user's instruction entered from the input circuitry 45. The tube current setting circuitry 41 may also be configured such that the imaging volume to be corrected is determined in accordance with the predetermined subject insertion direction. The subject insertion direction is a direction in which subject S is inserted in the opening of the gantry 10. For example, where subject S is inserted in the opening from the head, the subject insertion direction is defined as a head direction. Where subject S is inserted from the legs, the subject insertion direction is defined as a leg direction. The subject insertion direction is selected by the user and the related instruction is entered from the input circuitry 45 when an imaging plan is selected.

A detailed description will be given as to how an imaging volume to be corrected is automatically set in accordance with the subject insertion direction. The tube current setting circuitry 41 automatically select an imaging volume corresponding to the subject insertion direction based on a reference volume, and sets the selected imaging volume as a correction target. Let us assume that imaging is performed for the head and the subject insertion direction is the head direction. In many cases, the vertex head portion is of interest, as compared to the cranial head portion. Therefore, the tube current setting circuitry 41 select an imaging volume located closer to the vertex head portion than a reference volume, and sets the selected imaging volume as a correction target. For example, in FIG. 12, if imaging volume 3 is a reference volume, then imaging volumes 1 and 2 are set as correction targets.

After the imaging volumes are set as correction targets, the tube current setting circuitry 41 correct the tube current values in accordance with Step S6, with the imaging volumes being limited to the correction targets. Step S6 is not performed for the imaging volumes other than the correction targets. In this case, the tube current values of the imaging volumes other than the correction targets may be the initial tube current values which the tube current setting circuitry 41 determine in Step S4.

According to application example 3, the tube current values are corrected only with respect to imaging volumes which are included in a plurality of imaging volumes and which are set as correction targets. As compared with the case where the tube current values are corrected for all imaging volumes, the tube current value required by the correction of the tube current values can be reduced.

As described above, the present embodiment provides an X-ray computed tomography apparatus which automatically determines a tube current based on an X-ray absorption index value and which enables reduction of an image SD difference between imaging regions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit.

The invention claimed is:

1. An X-ray computed tomography apparatus, comprising:
   a gantry configured to emit X-rays from an X-ray tube to a plurality of imaging regions arranged in a body axis direction and detect X-rays emitted from the X-ray tube and transmitted through a subject by an X-ray detector; and
   a tube current setting circuitry configured to set a tube current for each of the imaging regions, wherein the tube current setting circuitry is configured to
   calculate first X-ray absorption index values representing amounts of X-rays absorbed by the subject in the respective imaging regions, based on scanogram image data on the subject in predetermined imaging directions,
   determine tube current values corresponding to the X-ray absorption index values for the respective imaging regions, and
   correct the tube current values of the respective imaging regions, except for a reference imaging region, based on a relative relationship between an X-ray absorption index value of the reference imaging region and the X-ray absorption index values of the other imaging regions.

2. The X-ray computed tomography apparatus according to claim 1, wherein the tube current setting circuitry is further configured to set a certain imaging region included in the imaging regions and having a largest first X-ray absorption index value as the reference imaging region.

3. The X-ray computed tomography apparatus according to claim 1, wherein the tube current setting circuitry is further configured to determine a weight value corresponding to a difference between the first X-ray absorption index value of the reference imaging region and the first X-ray absorption index values of the other imaging regions, and correct the tube current values of the other imaging regions in accordance with the determined weight value.

4. The X-ray computed tomography apparatus according to claim 3, wherein the tube current setting circuitry is further configured to
   calculate second X-ray absorption index values with respect to a plurality of pixels included in the other imaging regions,
   calculate first X-ray absorption index values of the other imaging regions, calculate a plurality of weighted second X-ray absorption index values by applying a weight value representing a difference between the second X-ray absorption index values and the first X-ray absorption index values of the reference imaging region, and
   correct the tube current values of the other imaging regions, based on the weighted second X-ray absorption index values.

5. The X-ray computed tomography apparatus according to claim 1, wherein the tube current setting circuitry is further configured to determine a weight value in accordance with distances between the reference imaging region and the other imaging regions, and correct the tube current values in accordance with the determined weight value.

6. The X-ray computed tomography apparatus according to claim 5, wherein the tube current setting circuitry is further configured to
   calculate a plurality of second X-ray absorption index values with respect to a plurality of pixels included in the other imaging regions,
   calculate an average value of the second X-ray absorption index values as the first X-ray absorption index values of the other imaging regions,
   calculate a plurality of weighted second X-ray absorption index values by applying the weight value determined in accordance with distances between the reference imaging region and the other imaging regions to the second X-ray absorption index values, and
   correct the tube current values of the other imaging regions, based on the weighted second X-ray absorption index values.

7. The X-ray computed tomography apparatus according to claim 1, wherein the tube current setting circuitry is further configured to control a difference between an uncorrected tube current value and a corrected tube current value to be a value determined in accordance with an imaging region.

8. The X-ray computed tomography apparatus according to claim 1, wherein the tube current setting circuitry is further configured to apply an initial modulation degree with reference to a first reference tube current value based on the first reference tube current value, to a plurality of imaging directions in each of the imaging regions, maintain the initial modulation degree with respect to an imaging direction in which X-rays have little effect on the subject, and change the initial modulation degree to a modulation degree with reference to a second reference tube current value based on the corrected tube current value, with respect to an imaging direction in which X-rays have an effect on the subject.

9. The X-ray computed tomography apparatus according to claim 1, wherein the tube current setting circuitry is further configured to determine water-equivalent thicknesses based on the first X-ray absorption index values, and determine tube current values corresponding to determined water-equivalent thicknesses.

10. The X-ray computed tomography apparatus according to claim 1, wherein the gantry performs CT imaging of the subject with respect to the imaging regions in accordance with the tube current values corrected by the tube current value setting circuitry.

11. The X-ray computer tomography apparatus according to claim 1, wherein the tube current setting circuitry is further configured to calculate a plurality of second X-ray absorption index values with respect to a plurality of pixels included in the imaging regions, determine weight values of second X-ray absorption index values such that the weight values are greater at positions where the X-rays are not hard than at positions where the X-rays are hard due to a heel effect, and calculate the first X-ray absorption index values based on a plurality of second X-ray absorption index values to which the weight values are applied.

12. The X-ray computer tomography apparatus according to claim 11, wherein the weight values determined by the tube current setting circuitry are larger for those pixels located far from an anode of the X-ray tube in a body axis direction and are smaller for those pixels located near the anode in the body axis direction.

13. The X-ray computer tomography apparatus according to claim 1, wherein the tube current setting circuitry is further configured to correct the tube current values only in an imaging region included in the imaging regions and which is a correction target region.

14. The X-ray computer tomography apparatus according to claim 13, wherein the tube current setting circuitry is further configured to set an imaging region included in the imaging regions and being of clinical interest as the correction target region.

15. The X-ray computer tomography apparatus according to claim 13, wherein the tube current setting circuitry is further configured to set the correction target region in accordance with a predetermined subject insertion direction.

* * * * *